(12) United States Patent
Whitmore, III

(10) Patent No.: US 7,316,663 B2
(45) Date of Patent: Jan. 8, 2008

(54) URETERAL STENT

(75) Inventor: Willet F. Whitmore, III, Sarasota, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 581 days.

(21) Appl. No.: 10/883,786

(22) Filed: Jul. 6, 2004

(65) Prior Publication Data

US 2004/0249470 A1    Dec. 9, 2004

Related U.S. Application Data

(62) Division of application No. 09/850,459, filed on May 7, 2001, now Pat. No. 6,764,519.

(60) Provisional application No. 60/207,607, filed on May 26, 2000.

(51) Int. Cl.
*A61M 37/00* (2006.01)
(52) U.S. Cl. .......................... 604/8; 623/23.7
(58) Field of Classification Search .............. 604/8, 604/9; 600/300; 623/23.64–23.7, 1.31, 623/1.32
See application file for complete search history.

(56) References Cited

U.S. PATENT DOCUMENTS

| | | |
|---|---|---|
| 3,783,454 A | 1/1974 | Sausse et al. |
| 3,938,529 A | 2/1976 | Gibbons |
| 3,995,642 A | 12/1976 | Adair |
| 4,212,304 A | 7/1980 | Finney |
| 4,225,979 A | 10/1980 | Rey et al. |
| 4,307,723 A | 12/1981 | Finney |
| 4,334,327 A | 6/1982 | Lyman et al. |
| 4,531,933 A | 7/1985 | Norton et al. |
| 4,551,137 A | 11/1985 | Osborne |
| 4,610,657 A | 9/1986 | Densow |
| 4,643,716 A | 2/1987 | Drach |

(Continued)

FOREIGN PATENT DOCUMENTS

EP    0 808 611 A3    12/1999

(Continued)

OTHER PUBLICATIONS

Hepperlen et al., "Self-Retained Internal Ureteral Stents: A New Approach," The Journal of Urology, Jun. 1978, vol. 119, pp. 731-734.

(Continued)

*Primary Examiner*—William H. Matthews

(57) ABSTRACT

A ureteral stent is designed to be placed within a patient's ureter to facilitate drainage from the patient's kidneys to the bladder. An elongated portion of the stent includes a length sufficient to extend substantially within the ureter from the kidney to the bladder, and the elongated portion defines a lumen extending therethrough. A retention portion extends from one end of the elongated portion and retains the position of the ureteral stent when placed substantially within the kidney. The retention portion includes an interior space that is in communication with the lumen within the elongated portion and has at least one opening for urine drainage. A flared portion extending from the other end of the elongated portion is positioned within the patient's bladder. The flared portion curves outward and includes an elastic member that maintains the shape of the flared portion when positioned within the bladder.

17 Claims, 10 Drawing Sheets

U.S. PATENT DOCUMENTS

| | | |
|---|---|---|
| 4,671,795 A | 6/1987 | Mulchin |
| 4,713,049 A | 12/1987 | Carter |
| 4,785,059 A | 11/1988 | Fydelor et al. |
| 4,787,884 A | 11/1988 | Goldberg |
| 4,790,809 A | 12/1988 | Kuntz |
| 4,790,810 A | 12/1988 | Pugh, Jr. et al. |
| 4,790,816 A | 12/1988 | Sundblom et al. |
| 4,813,925 A | 3/1989 | Anderson, Jr. et al. |
| 4,820,262 A | 4/1989 | Finney |
| 4,874,360 A | 10/1989 | Goldberg et al. |
| 4,913,683 A | 4/1990 | Gregory |
| 4,931,037 A | 6/1990 | Wetterman |
| 4,950,228 A | 8/1990 | Knapp, Jr. et al. |
| 4,957,479 A | 9/1990 | Roemer |
| 4,990,133 A | 2/1991 | Solazzo |
| 4,990,228 A | 2/1991 | Perusich et al. |
| 5,019,102 A | 5/1991 | Hoene |
| 5,078,684 A | 1/1992 | Yasuda |
| 5,116,309 A | 5/1992 | Coll |
| 5,141,502 A | 8/1992 | Macaluso, Jr. |
| 5,176,626 A | 1/1993 | Soehendra |
| 5,221,253 A | 6/1993 | Coll |
| 5,224,953 A | 7/1993 | Morgentaler |
| 5,246,445 A | 9/1993 | Yachia et al. |
| 5,269,802 A | 12/1993 | Garber |
| 5,282,784 A | 2/1994 | Willard |
| 5,346,467 A | 9/1994 | Coll |
| 5,354,263 A | 10/1994 | Coll |
| 5,364,340 A | 11/1994 | Coll |
| 5,401,257 A | 3/1995 | Chevalier, Jr. et al. |
| 5,514,176 A | 5/1996 | Bosley, Jr. |
| 5,520,697 A | 5/1996 | Lindenberg et al. |
| 5,531,741 A | 7/1996 | Barbacci |
| 5,599,291 A | 2/1997 | Balbierz et al. |
| 5,647,843 A | 7/1997 | Mesrobian et al. |
| 5,681,274 A | 10/1997 | Perkins et al. |
| 5,684,051 A | 11/1997 | Thompson |
| 5,782,916 A | 7/1998 | Pintauro et al. |
| 5,795,319 A | 8/1998 | Ali |
| 5,814,006 A | 9/1998 | Planz |
| 5,921,952 A | 7/1999 | Desmond, III et al. |
| 5,964,744 A | 10/1999 | Balbierz et al. |
| 5,971,967 A | 10/1999 | Willard |
| 6,013,102 A | 1/2000 | Pintauro et al. |
| 6,053,941 A | 4/2000 | Lindenberg et al. |
| 6,059,808 A | 5/2000 | Boussignac et al. |
| 6,139,536 A | 10/2000 | Mikus et al. |
| 2003/0171708 A1 | 9/2003 | Segura et al. |

FOREIGN PATENT DOCUMENTS

| | | |
|---|---|---|
| WO | WO 97/17094 | 5/1997 |
| WO | WO 00/66032 | 11/2000 |
| WO | WO 01/89415 | 11/2001 |
| WO | WO 01/91668 | 12/2001 |
| WO | WO 03/075795 | 9/2003 |

OTHER PUBLICATIONS

Collier et al., "Proximal Stent Displacement as Complication of Pigtail Ureteral Stent," Urology, Apr. 1979, vol. XIII, No. 4, pp. 372-375.

Mardis et al., "Polyethylene Double-Pigtail Ureteral Stents," Urologic Clinics of North America, Feb. 1982, vol. 9, No. 1, pp. 95-101.

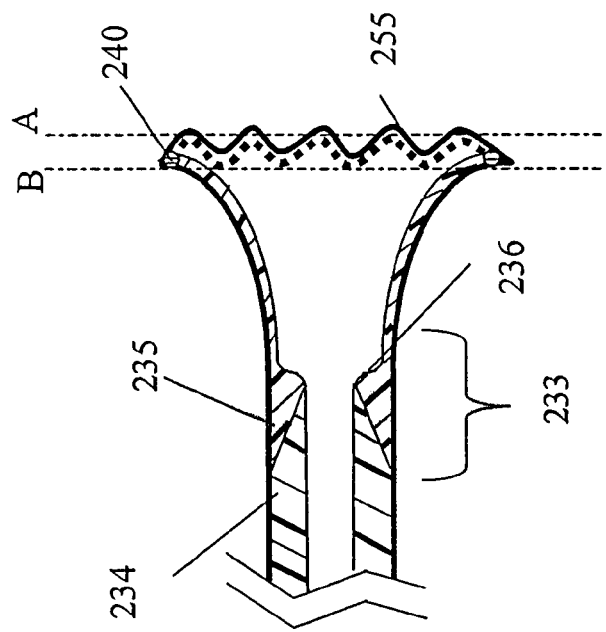
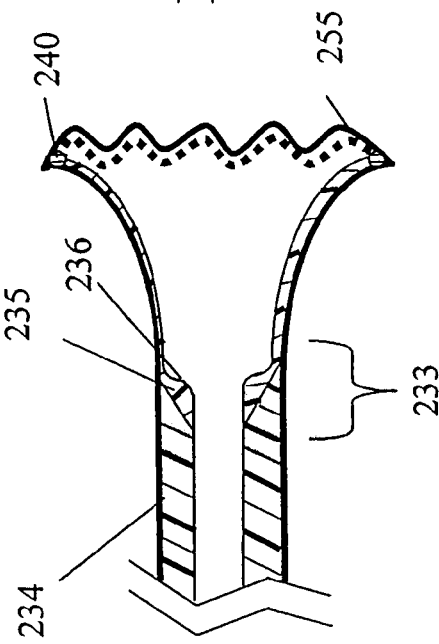
FIG. 2E
FIG. 2F

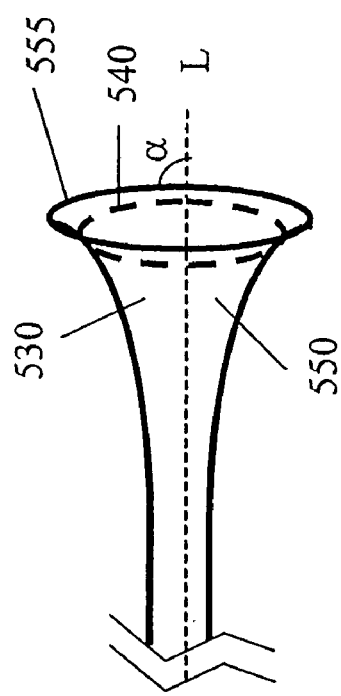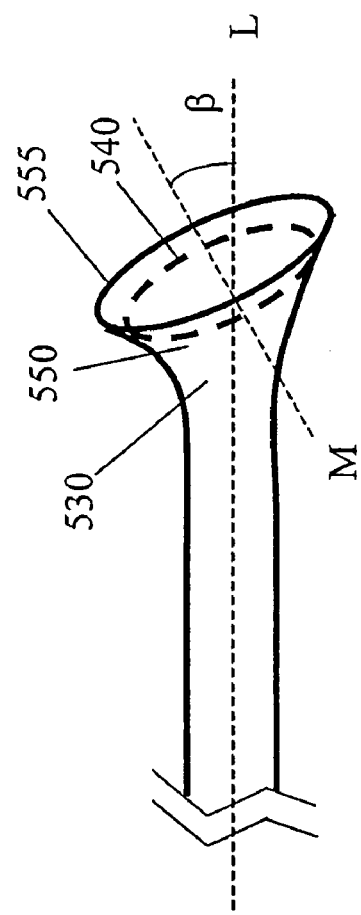

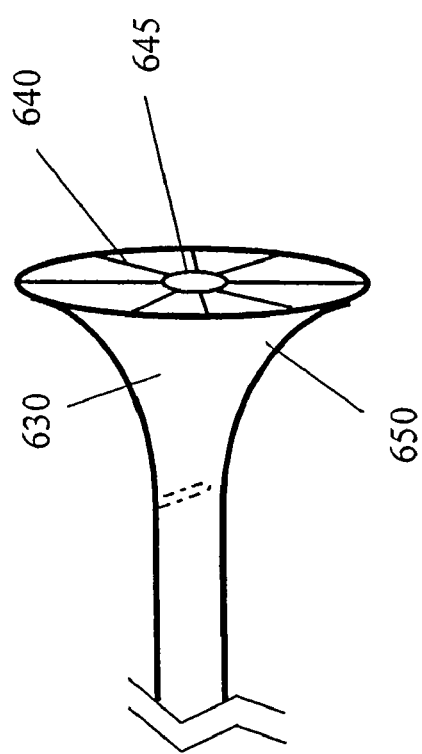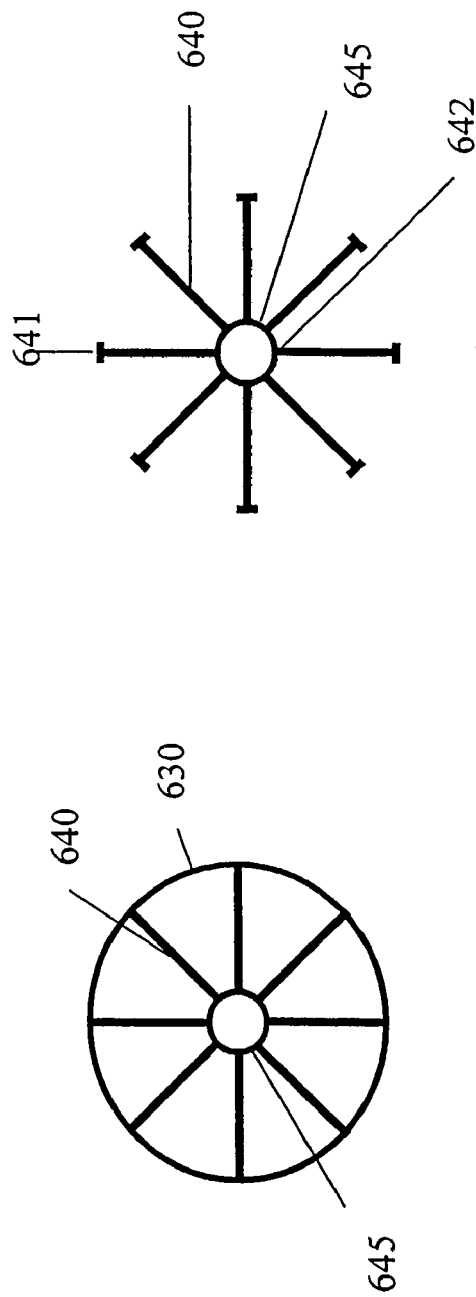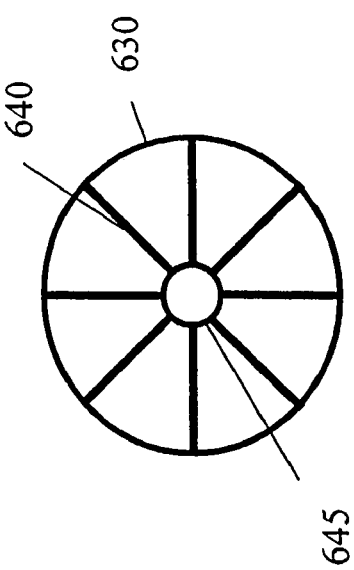

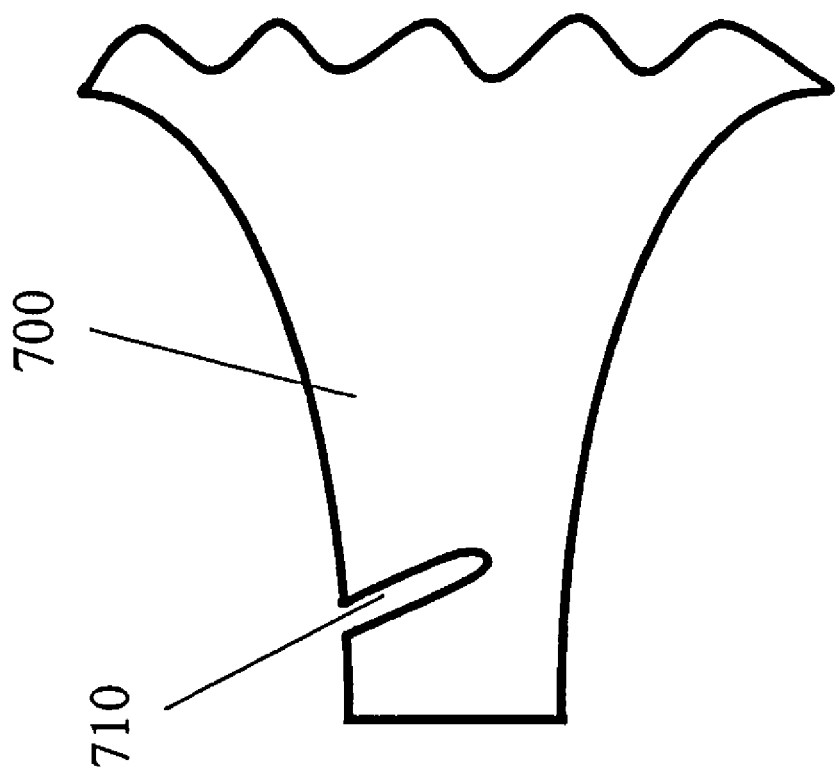

URETERAL STENT

CROSS-REFERENCE TO RELATED CASE

This application is a divisional application of application Ser. No. 09/850,459, filed May 7, 2001 now U.S. Pat. No. 6,764,519, the entire content of which is hereby incorporated by reference, which claims priority to and the benefit of U.S. provisional patent application Ser. No. 60/207,607, filed on May 26, 2000, the entirety of which is incorporated herein by reference.

TECHNICAL FIELD

This invention relates to stents and methods of maintaining patency of a body lumen such as the ureter using stents.

BACKGROUND INFORMATION

A ureter is a tubular passageway in a body that conveys urine from a kidney to a bladder. Urine is transported through the ureter under the influence of hydrostatic pressure assisted by contractions of muscles located within the walls (lining) of the ureter. A urological condition that some patients experience is ureteral blockage or obstruction. Some common causes of ureter blockage are the formation of tumors or abnormalities within the ureteral lining or the formation and passage of kidney stones.

Ureteral stents are medical devices designed to extend through the ureter and are frequently used to bypass the ureter to facilitate drainage from a kidney to the bladder when a ureter becomes blocked or obstructed. Generally, these stents are made from small diameter tubing of a biocompatible plastic. Ureteral stents may have multiple side holes to enhance drainage and typically include retention hooks, pigtail curls, coils, or malecots extending from both the kidney (distal) and bladder (proximal) ends of the tubing to prevent the migration of the ureteral stent after placement within the ureter.

SUMMARY OF THE INVENTION

The present invention generally relates to draining fluids from the kidney to the bladder of a patient with a stent. Devices and methods according to the invention are typically used in the treatment of patients suffering from an obstructed ureter to address and relieve urinary retention while minimizing patient discomfort. It is an object of the invention to maintain the ureter open and able to pass fluids from the kidney to the bladder. It is another object of the invention to minimize patient discomfort.

In one aspect, the invention relates to a ureteral stent. The ureteral stent includes an elongated portion, a retention portion extending from one end of the elongated portion, and a flared portion extending from the other end of the elongated portion. The elongated portion has a length sufficient to extend substantially within the ureter from the kidney to the bladder and defines a lumen extending within. The retention portion extends from a distal end of the elongated portion and is configured for placement and retention within the kidney. The retention portion includes an interior space in communication with the lumen of the elongated portion and at least one opening in communication with the interior space for urine drainage from the kidney to the ureteral stent. The flared portion extends from a proximal end of the elongated portion and is configured for placement substantially within the bladder. The flared portion curves outward while extending from the elongated portion and includes an elastic member for maintaining the shape of the flared portion in an expanded shape when located within the bladder. The flared portion is collapsible to allow entry of the flared portion into the bladder through the urethra.

Embodiments of this aspect of the invention can include the following features. For example, the elastic member of the flared portion may be made from a shape-memory material or a superelastic material, such as for example, a nickel-titanium alloy, or an elastomeric material. In some embodiments, the elastic member is a ring or loop of material that is embedded within or attached to the flared portion. The shape of the ring or loop may be round, oval, or even elliptical, or it may even be patterned to have a sinusoidal or saw-tooth shape. In other embodiments, the elastic member may include a plurality of collapsible spokes. These collapsible spokes have a first and a second end. The first end of the spokes is attached to a wall of the flared portion and the second end is attached to a hub. In an expanded state, the spokes extend radially from the hub. In a collapsed state, the spokes extend longitudinally from the hub.

In some embodiments, the flared portion may further include a valve that allows fluid to pass from the elongated portion through the valve, out of the flared portion, and into the bladder, but not from the bladder back into the elongated portion. The flared portion itself is made from a thin flexible material and may be corrugated. The retention portion, which is located within the kidney when the ureteral stent is placed within the patient, may be made from a shape-memory or a superelastic material and may have a coil or other retention structure shape. In other embodiments, the entire ureteral stent including the elongated portion, the retention portion, and the flared portion is sized to fit within a cystoscope.

In general, in another aspect, the invention features a method of inserting within a urinary tract a ureteral stent such as the stent described above. The method includes inserting the stent into the urinary tract of a patient and positioning the ureteral stent within the ureter of the patient such that the retention portion is within the kidney and the flared portion is within the bladder. The method may also include collapsing the flared portion of the ureteral stent prior to insertion and allowing the flared portion to expand within the bladder. The method may further include providing a cystoscope sized to receive the ureteral stent and using the cystoscope to insert and position the ureteral stent within the urinary tract of the patient.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2E is an enlarged cross-sectional view of a portion of the ureteral stent of FIG. 2A showing one embodiment of a transition between an elongated portion and the flared portion.

FIG. 2F is another enlarged cross-sectional view of a portion of the ureteral stent of FIG. 2A showing another embodiment of a transition between an elongated portion and the flared portion

FIG. 5A is an enlarged front view of another embodiment of a flared portion in an expanded configuration.

FIG. 5B is an enlarged front view of another embodiment of a flared portion in an expanded configuration.

FIG. 6A is an enlarged front view of another embodiment of a flared portion in an expanded configuration.

FIG. 6B is an enlarged side view of the flared portion of FIG. 6A also in an expanded configuration.

FIG. 6C is an enlarged view of a reinforcing member of the flared portion shown in FIGS. 6A and 6B.

FIG. 7 is a front view of a mold used to form the flared portion of FIG. 2C.

DESCRIPTION

Figure 1:
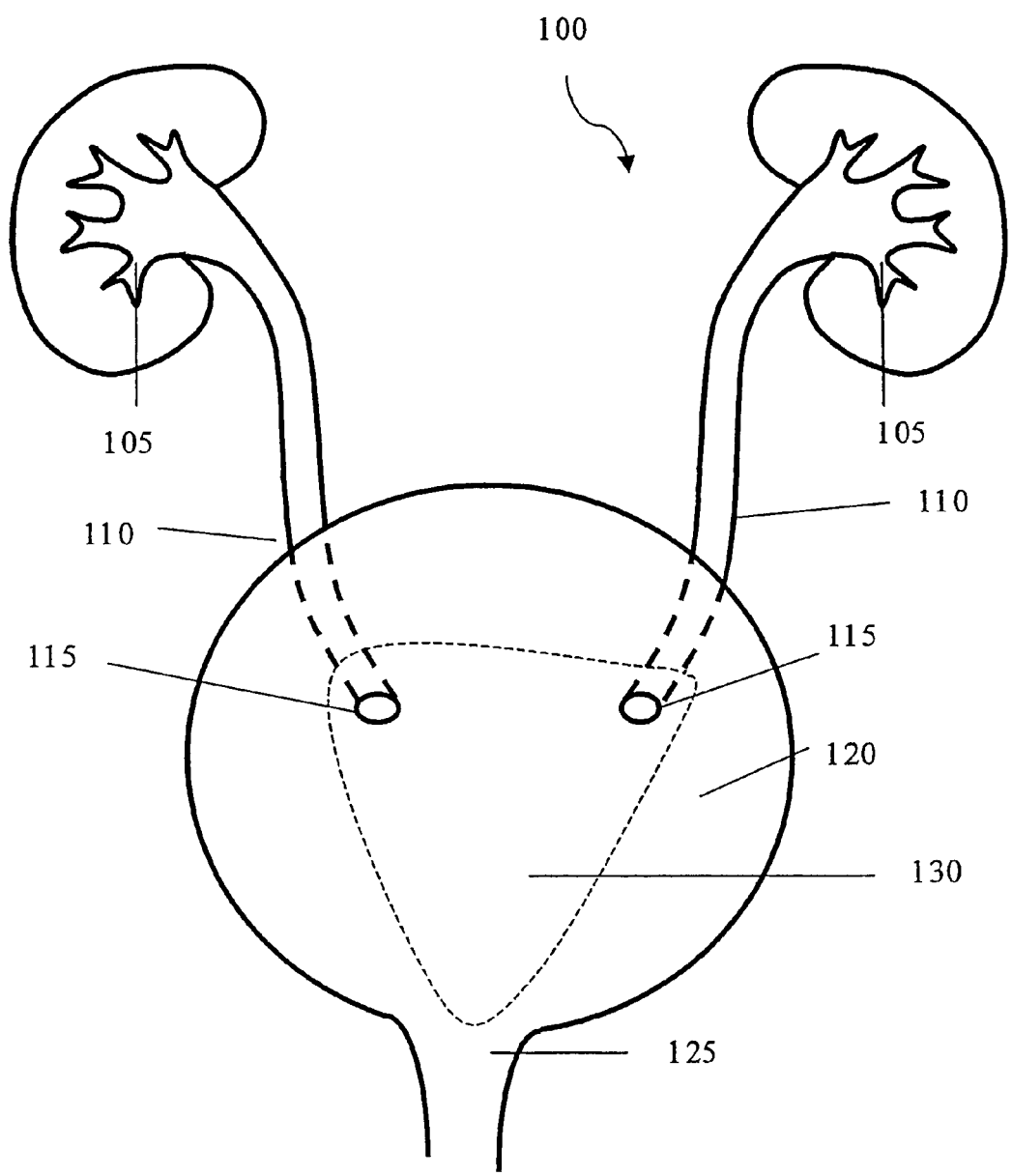
FIG. 1 is a schematic view of a human urinary tract.

Referring to FIG. 1, in a human urinary tract 100, the ureters 110 transport urine from the kidneys 105 to the bladder 120. When one or both of the ureters 110 become blocked or obstructed due to, for example, the growth of a tumor or the entrapment of a kidney stone, a temporary alternative path is needed to provide fluid drainage. Ureteral stents are medical devices that are implanted within the ureters 110 to restore their patency and fluid drainage. Conventional ureteral stents have pigtail or hook ends designed to retain the stent within the ureter. In the bladder, these retention structures contact the bladder lining within a sensitive area known as the trigone. The trigone 130 is a triangular section of the bladder 120 located between the urethral opening 125 and the two ureteral orifices 115. It is a sensitive region of the bladder that contains a nerve bed. Typically, foreign objects within the trigone rubbing against the bladder may stimulate this nerve bed causing the patient to experience urinary urgency sensations. Stimuli within the trigone are due to contact with the bladder end portion of these conventional stents and are believed to be the source of patient discomfort.

This invention generally concerns ureteral stents that, when positioned within the ureter of a patient, significantly reduce discomfort to the patient. The structure of ureteral stents according to the invention provides an increase in comfort for a patient, because the proximal or bladder portion of the ureteral stent is designed to minimize stimulation in the trigone.

To minimize stimulation of the nerves within the trigone, according to the invention, a portion of the stent that resides in the bladder has a horn shape design that flares or curves outward and is therefore referred to as a flared portion. The shape of the flared portion provides the ureteral stent of the present invention with broad, soft surfaces, which softly contact the end of the ureter where it enters the trigone. In ideal position, the shape will contact only this area and not contact other area of the trigone or of the bladder surface. The shape of the flared portion may be symmetrical along a longitudinal axis of the ureteral stent, as shown, for example, in FIG. 5A. Alternatively, the flared portion may be shaped such that a median axis of the flared portion is tilted with respect to the longitudinal axis of the stent, as shown, for example in FIG. 5B. The flared portion includes a wall that forms the horn shape. This wall may be smooth or corrugated. The wall includes a rim that defines the largest opening to the flared portion. To act as a retention structure, the rim, when expanded, has a size that is larger than the ureteral orifice. Generally, a normal ureter has a diameter size that may extend up to between about 2 millimeters and 6 millimeters. After dilation of the ureter, the ureter's diameter size may be further increased up to about 8 millimeters. Therefore the expanded diameter size of the rim should be 8 millimeters or larger to prevent the flared portion from migrating into the ureter and preferably, the diameter of the rim is sized in the range between about 9 millimeters to 12 millimeters. The rim may be smooth, or have a pattern according to the invention that is undulating or jagged. The rim may be symmetrical and have a generally overall round, oval, or elliptical shape. Alternatively, the rim may also be asymmetrical. The flared portion further decreases nerve stimulation within the trigone by providing only a small amount of material within the bladder. The flared portion is made from a thin flexible material that allows the flared portion to achieve a high surface area to contact pressure ratio as well as to contour and tilt naturally to conform to the shape of the ureteral orifice.

To reinforce the thin wall and maintain the shape of the flared portion expanded within the bladder, the flared portion further includes an elastic member. The elastic member may be embedded with the wall of the flared portion or attached to the rim such that, when the elastic portion is extended, the form of the flared portion resembles a trumpet or a horn.

Both the elastic member and the flared portion are collapsible to allow for insertion through the urethra to the bladder. Once located within the bladder, the elastic member springs back to its original and expanded state to reform and support the shape of the flared portion.

Suitable elastic members may take a variety of forms and shapes and a variety of positions within the flared portion. For example, the elastic member of the flared portion may be a loop of an elastic and resilient material. The loop may have a sinusoidal or saw-tooth wave pattern. Alternatively, the elastic member may include a center hub connected to collapsible spokes similar to the mechanism within an umbrella with the spokes attached at least to or near the rim of the horn.

Suitable material for the elastic member includes, but is not limited to rubbers, shape-memory alloys and superelastic materials. Both superelastic and memory-shape materials are well known materials that make it possible for a segment or portion to have a particular first shape that can be reversibly modified to a second shape. For example, it is possible to configure a segment of a superelastic material into a closed loop and then with the aid of a sheath collapse the loop temporarily during insertion and placement within a patient's body. Upon removing the sheath, the loop returns to the original radially expanded shape. A shape-memory material can also alternate between the first shape and the second shape. However, shape-memory materials rely on phase changes triggered by changes in temperature to produce the shape change. Generally, nickel-titanium alloys having a nickel composition within the range of about 50 to 53% transition from an elastic phase to a plastic phase at about normal human body temperature and are often used for various medical devices. Nickel-titanium alloys having a nickel composition greater than 53% may also be used to form elastic members or retention devices, if a heat source is provided to treat the material in vivo to produce the desired phase change.

The material that forms the thin flexible wall of the flared portion may be selected from any biocompatible polymer or plastic, such as, for example silicone or other PTFE polymers. The shape of the flared portion may be manufactured by dip molding, machining, thermosetting, or vacuforming. These along with other features of ureteral stents of the invention are described in further detail below.

Figure 2A:
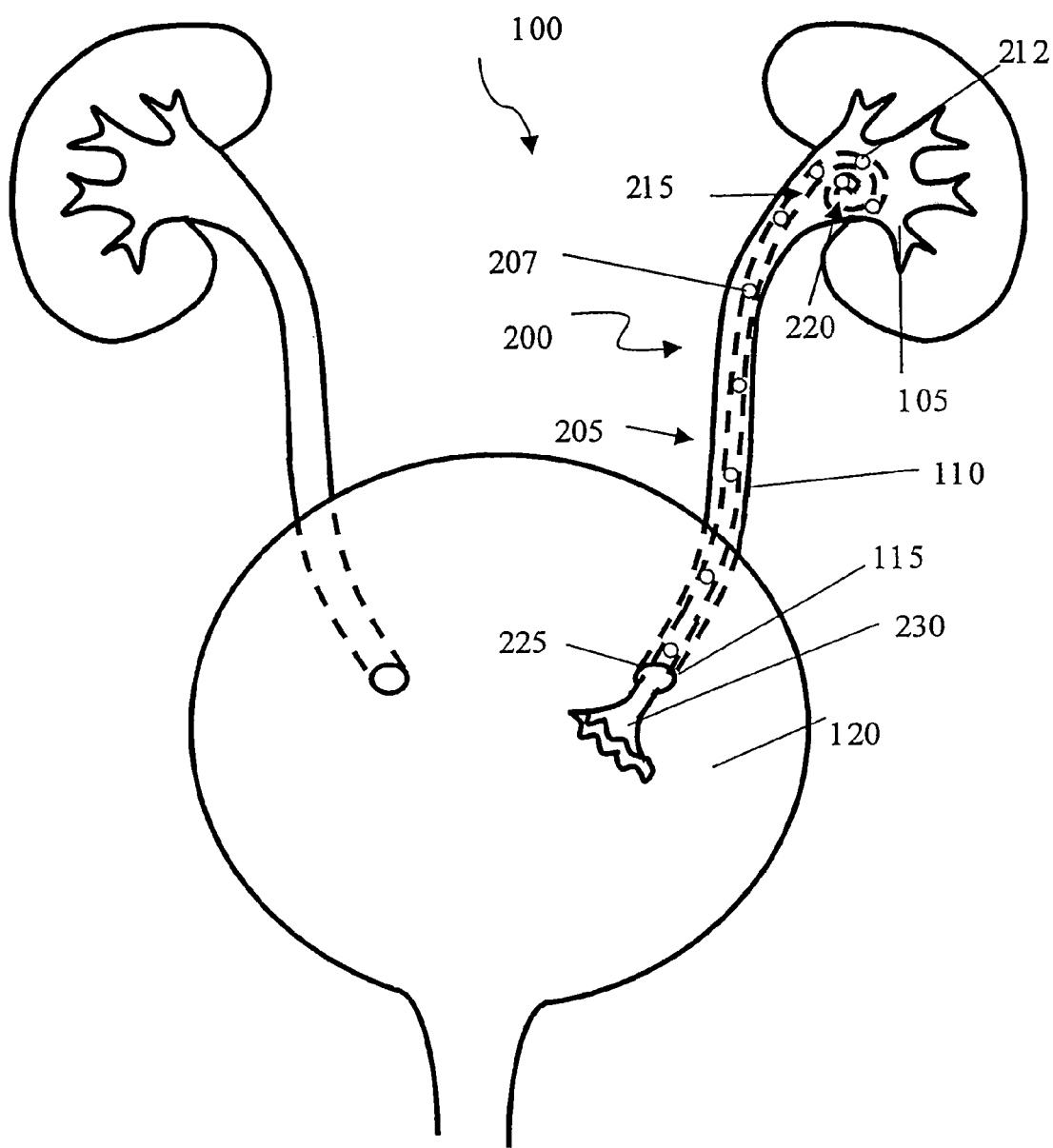
FIG. 2A is a schematic view of an embodiment of a ureteral stent according to the invention positioned within the human urinary tract.

Now referring to FIG. 2A, a ureteral stent 200 of the invention is located within the human urinary tract 100. The ureteral stent 200 includes an elongated portion 205 that spans between a retention portion 220 and a flared portion 230. The elongated, retention, and flared portions 205, 220, 230 are indicated generally in FIG. 2B. The elongated portion 205 extends substantially the entire length of one of the ureters 110 when placed within the urinary tract 100 of a patient and has a distal end 215 and a proximal end 225. Within the elongated portion 205, extending between the distal end 215 and the proximal end 225 is a passageway or a lumen for transporting bodily fluids, such as, for example, urine. Located along the length of the ureteral stent 200, as shown in FIG. 2A, can be a plurality of openings 207 in communication with the lumen. These openings 207 are optional, and if present tend to increase drainage of urine through the stent and into the bladder 120.

The retention and flared portions 220, 230 extend from the respective distal and proximal ends 215, 225 of the elongated portion 205 and have shapes designed to retain the ureteral stent 200 within the ureter 110 and thereby prevent migration of the ureteral stent 200. In the embodiment disclosed in FIG. 2A, the distal retention portion 220 is a pigtail coil that extends from the distal end 215 of the elongated portion 205. The retention portion 220 can be straightened to allow passage of the retention and elongated portions 220, 205 all the way through the ureter 110. Once the retention portion 220 is positioned within the kidney 105, the retention portion 220 is allowed to re-coil to anchor the ureteral stent 200 within the kidney 105, thereby preventing proximal migration of the stent and keeping the flared portion snug against the ureteral orifice. In some embodiments, the retention portion may be able to coil a self-adjustable number of turns to eliminate any excessive length of the elongated portion, thereby allowing the flared portion to remain snug against the ureteral orifice and permitting the stent to fit a greater range of ureter length. Alternatively, the distal retention portion may also be a hook, a malecot, or other structure that functions as an anchor to retain the ureteral stent 200 within the kidney 105. Within the retention portion 220, there is an interior space (an extension of the lumen of the elongated portion 205, in the disclosed embodiment) that is in communication with the lumen of the elongated portion 205. At least one opening 212 in communication with the interior space is present on the retention portion 220, such that urine or any other bodily fluid from the kidney 105 may enter this opening 212. After entering into the opening 212, fluid is carried through the interior space, down into the lumen of the elongated member 205.

The flared portion 230 extends and curves outward from the proximal end 225 of the elongated portion 205. The flared portion 230 is a floppy, horn-shaped structure that is designed not only to retain or anchor the proximal end 225 of the elongated portion 205 within the bladder 120, but also to minimize stimulation in the sensitive trigone 130. The horn shape of the flared portion 230 has soft, convex surfaces that contact areas only around the ureteral orifice 115. The flared portion 230 has an overall larger diameter than the ureter 110 and prevents the stent 200 from migrating or travelling into the ureter 110. The ureteral stent 200 achieves comfort for the patient by permitting only soft, flexible surfaces with a high surface area to contact pressure ratio to come in contact to sensitive bladder mucosal tissue, while achieving a desirable small total contact surface area in the bladder 120. The flared portion 230 contacts the bladder 120 only in the area near the ureteral orifice 115, and not elsewhere within the trigone 130. Pressure on the bladder from contact with the flared portion 230 is distributed over a larger surface area compared to traditional proximal retention devices, such as, for example, a pigtail coil and is thus gentler and less irritating to the patient.

Figure 2B:
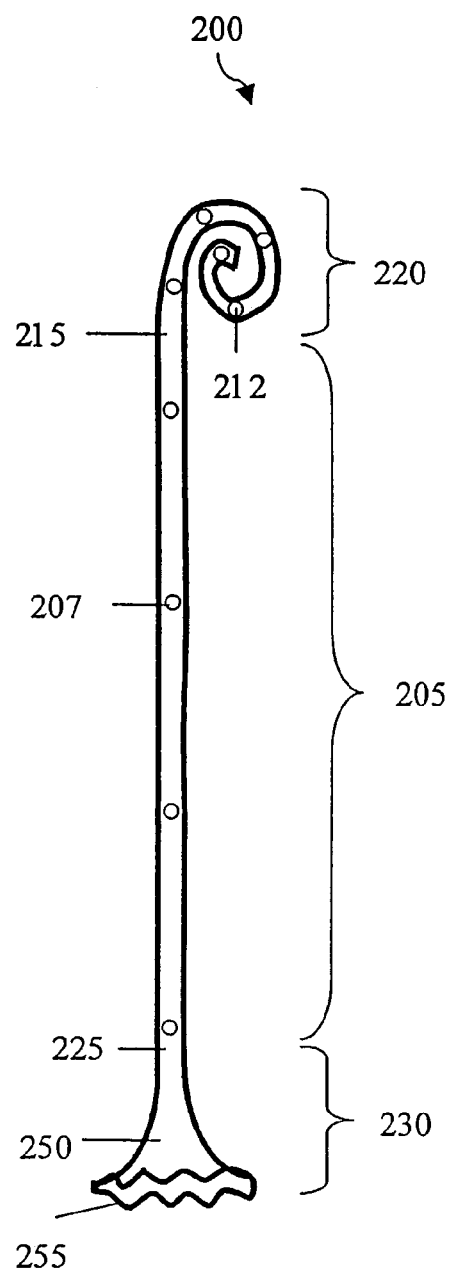
FIG. 2B is a front view of the ureteral stent of FIG. 2A.
Figure 2C:
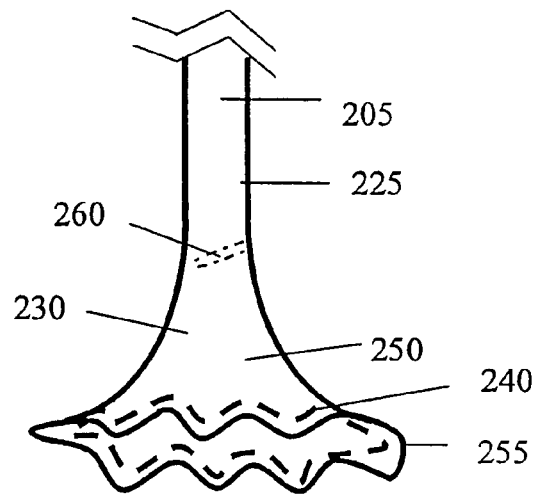
FIG. 2C is an enlarged front view of one embodiment of a flared portion of the ureteral stent of FIG. 2A in an expanded configuration.
Figure 2D:
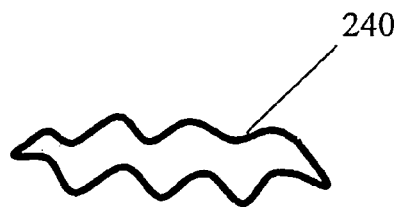
FIG. 2D is a front view of one embodiment of an elastic member.

Referring to FIGS. 2B and 2C, the flared portion 230 has a smooth wall 250 defining the flared, horn shape and an elastic member 240 that is either embedded within or attached to the wall 250 near its rim 255. The wall 250 is made from a flexible, biocompatible material, such as, for example, silicone and has a substantially thin wall thickness, such that the wall 250 is floppy and easily compressible. In FIGS. 2A-2C, the elastic member 240 has an undulating (sinusoidal) annular shape and is disposed near the rim 255. The elastic member 240 may be embedded within the wall 250 of the flared portion 230, as shown in FIG. 2C. Alternatively, in other embodiments, the elastic member may be glued or mechanically fastened to either the inside or outside of the wall 250. The elastic member 240 is shown by itself in FIG. 2D and may be made from an elastomer, such as, for example, rubber or other polybutadienyl material, or from a shape-memory alloy, such as, for example, a nickel-titanium alloy. The elastic member 240 may be expanded and collapsed and is biased towards an expanded state. The elastic member 240 will return to the expanded state in the absence of external forces acting upon it. In the expanded state, the elastic member 240 supports and maintains the flared, horn shape of the wall 250. In the collapsed state, the elastic member 240 has a perimeter substantially equivalent to a perimeter of the elongated portion 205 to facilitate insertion through the urethra.

In some ureteral stents, a back-flow of urine can occur during voiding and generally results in patient discomfort. To increase patient comfort, the flared portion 230 may also include a valve 260 to prevent urine from traveling up the ureter 110 from the bladder to the kidneys. In the disclosed embodiment, the valve 260 is a flap of flexible material that extends within the flared portion 230 across the lumen of the elongated portion 205. The valve 260 is located near the proximal end 225 of the elongated portion 205 and is sized such that in the absence of fluid flowing down from the lumen of the elongated portion 205 the flap substantially blocks the distal end 225. Thus, as long as urine is flowing antegrade under the influence of normal hydrostatic pressure, the valve will remain open and will allow the urine to pass from the kidney to the bladder. However, urine already located within the bladder substantially can not re-enter the kidney because the valve 260 blocks the lumen in distal end 225 of the elongated portion 205, thereby preventing urine from travelling up the ureteral stent 200 if the pressure relationships are reversed preventing retrograde flow.

Because of its thin wall, the flared portion 230 has a less amount of material (compared to a structure with a greater wall thickness) with which to stimulate the nerves within the trigone. The remainder of the stent (i.e., the elongated portion and the retaining portion) may be made of thicker material to provide stability and structural integrity such that it resists buckling and kinking. The elongated portion 205 requires a certain amount of stiffness to maintain patency through an obstructed ureter. The wall thickness transitions from a thin wall in the flared portion 230 to a thicker wall in the elongated portion 205 in a transition zone 233. This transition can be accomplished by increasing the wall thickness in the transition zone 233 from the flared portion 230 through the distal end 225 of the elongated portion 205, by using a different material to form the elongated portion that has a greater durometer than the flared portion, or by a combination of both.

FIGS. 2E and 2F show cross-sectional views of the transition zone 233 between the flared portion 230 and the elongated portion 205. In these two figures, the transition in stiffness is accomplished by increasing the wall thickness and providing two different materials for the flared portion 230 and the elongated portion 205. The material selected for the elongated portion 205 should have a greater durometer than the material selected for the flared portion 230, thereby providing the elongated portion 205 with a greater stiffness to maintain patency through an obstructed ureter. Within the transition zone 233, the stiffness gradually increases due to the dovetailing of tapered proximal end portion 234 of the elongated portion 205 and tapered distal end portion 235 of the flared portion 230. In FIG. 2E, the inner wall of the flared portion tapers from an inner diameter the size of the lumen to the outer diameter of the elongated portion. In FIG. 2F, the outer wall of the flared portion tapers from the outer diameter of the elongated portion to the inner diameter of the lumen. In both embodiments, a pusher landing area 236 is created at the proximal end of their junction. When the elongated portion 205 and the flared portion 230 are formed from different materials, as shown in FIGS. 2E and 2F, the elongated and flared portions 205, 230 may be joined either by a gluing, molding, or mechanically fastening the two portions together. If a mechanical fastener is used, it may be embedded within the walls of the elongated and flared portion so as not to directly contact the ureter or the bladder or obstruct the lumen.

Figure 3A:
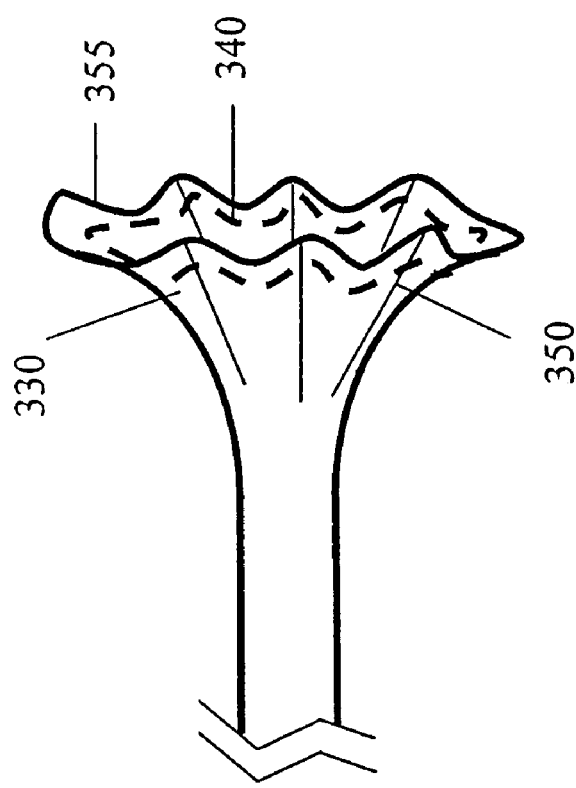
FIG. 3A is an enlarged front view of another embodiment of a flared portion in an expanded configuration.
Figure 3B:
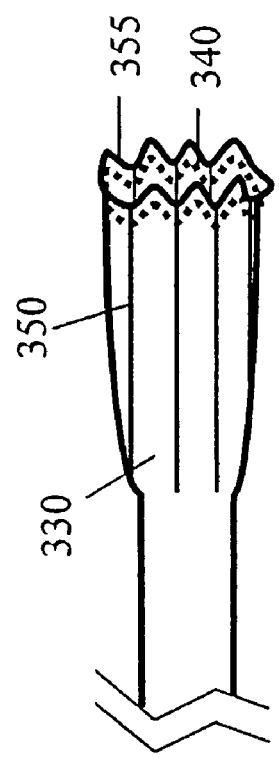
FIG. 3B is an enlarged front view of the flared portion of FIG. 3A in an insertion/collapsed configuration.
Figure 4A:
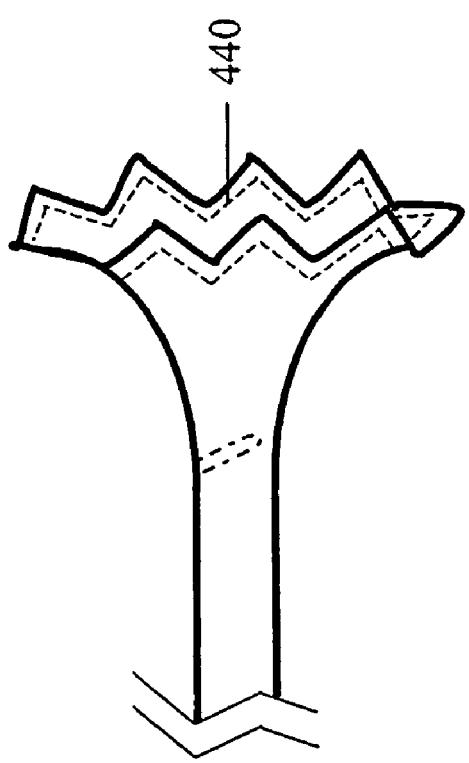
FIG. 4A is an enlarged front view of another embodiment of a flared portion in an expanded configuration.
Figure 4B:
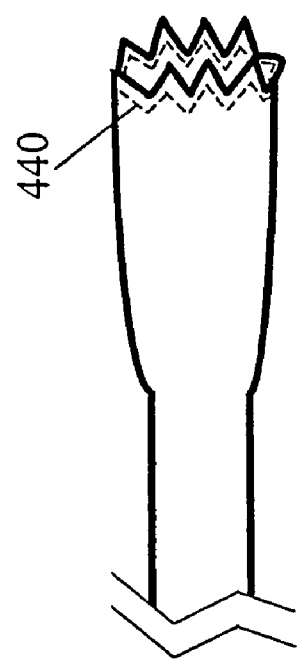
FIG. 4B is an enlarged front view of the flared portion of FIG. 4A in an insertion/collapsed configuration.
Figure 6D:
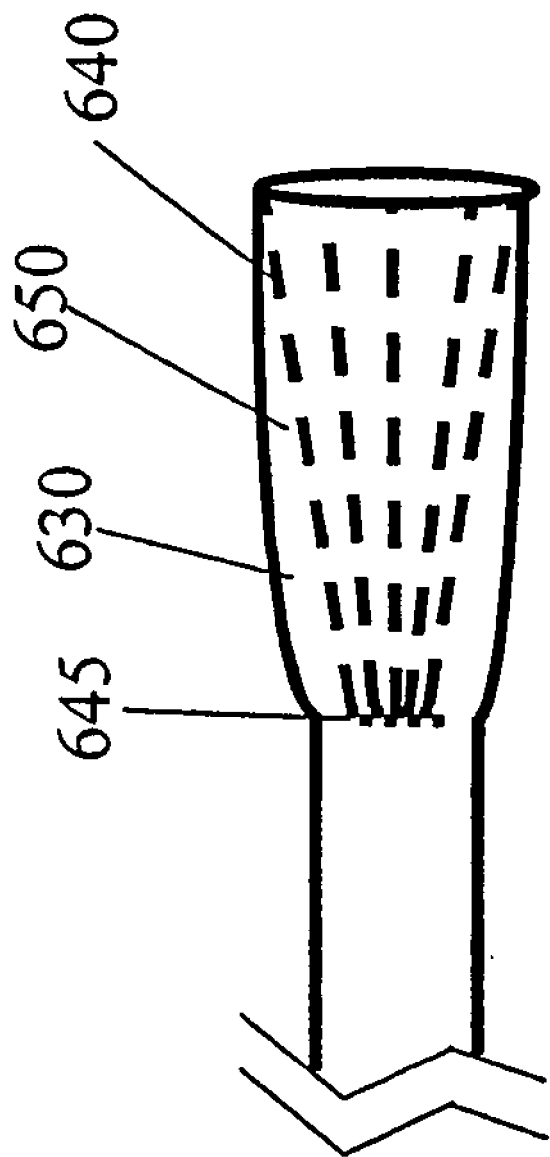
FIG. 6D is an enlarged front view of the flared portion of FIG. 6A in an insertion or collapsed configuration.

The flared portion 230, in FIGS. 2A-2F, has a sinusoidal looped elastic member 240 embedded within the wall 250 that maintains the shape of the flared portion 230 when the elastic member 240 is in the expanded state. The sinusoidal pattern of the elastic member 240 undulates along the wall 250 of the flared portion 230 between a proximal transverse plane A and a distal transverse plane B as shown in FIG. 2E. When expanded, the elastic member 240 maintains the flared horn shape of the wall 250 wide open. When collapsed, the perimeter of the elastic member 240 is sized to permit insertion and travel through the human urinary tract 100. Because the elastic member 240 is either embedded or attached to the wall 250 of the flared portion 230, when the elastic member 240 is collapsed, the flared portion 230 and the wall 250 are collapsed as well. As the flared portion 230 collapses, the wall 250 folds to accommodate the size of the collapsed elastic member 240. The sinusoidal shape of the looped elastic member 240 prevents excess pre-folding of the wall 250 and is desirable because folding can lead to deformation or crimping of the wall 250 over itself. In FIGS. 2A-2F, the wall 250 of the flared portion is smooth. In some embodiments, the wall of the flared portion may be corrugated as shown in FIGS. 3A and 3B to further aid in the collapse of a flared portion. FIG. 3A shows a flared portion 330 having a sinusoidal looped elastic member 340 in the expanded state embedded within a wall 350 near the rim 355 made of a corrugated, flexible material. Alternatively, the pattern of the elastic member need not be sinusoidal to limit the amount of folding needed to collapse the wall of the flared portion, as any other waving pattern would provide sufficient yield to radial constriction. In other embodiments, an elastic member 440 may have, for example, a saw-tooth pattern as shown in FIGS. 4A and 4B.

In some embodiments of the present invention, the elastic member may be a smooth planar loop and is collapsed radially and folded longitudinally for ease of insertion. Referring to FIGS. 5A and 5B, an elastic member 540 of a flared portion 530 has a curvilinear shape and embedded within the wall 550 near the rim 555. The elastic member 540 forms a loop that includes more than one focal point of curvature, such as, for example, an ellipse or an oval. The elastic member 540 may be expanded or collapsed, and is biased towards an expanded state. The plane of the loop (elastic member 555) forms an angle $\alpha$ of 90 or less degrees with a longitudinal axis L of the elongated portion 205. To prevent longitudinal folding of the wall 550 while the elastic element 540 is collapsed and folded over the length of the flared portion, the flared portion 530 may be tilted such that a median axis M of the flared portion 530 forms an angle $\beta$ with the longitudinal axis L of the elongated portion 205 as shown in FIG. 5B.

Referring to FIGS. 6A-6D, alternatively, a wall 650 of flared portion 630 may be maintained in an expanded state with a plurality of spokes 640. The spokes 640 have a first end 641 and a second end 642. The first end 641 of the spokes 640 is attached to the wall 650. The second end 642 is attached to a center hub 645. The spokes 640 are collapsible and expandable and may be made from a shape-memory alloy or a superelastic material, such as, for example, a nickel-titanium alloy. When the spokes 640 are expanded, the spokes 640 extend radially out from the hub 645 and thus support the flared, horn shape of the wall 650. When the spokes 640 are collapsed, as in FIG. 6D, the spokes 640 extend longitudinally from the hub 645 and the wall 650 folds to accommodate the collapsed spokes 640.

All of the flared portions described above provide comfort to a patient because they are all designed to minimize stimulation within the trigone of the bladder. The flared portions of the present invention, while so designed are simultaneously designed to anchor the ureteral stent within the bladder so as to prevent migration of the stent up the ureter towards the kidney. Ureteral stents, devices that maintain patency from the kidneys to the bladder that include the flared portions as described herein will provide patients with increased comfort.

Various techniques, such as, for example, machining, injection molding, dip molding, and thermosetting may be used to manufacture the flared portion of the present invention. To machine a flared portion, a material such as, for example, a hydrophilic monomer that changes its mechanical characteristics from rigid to elastic with hydration may be utilized to produce the wall of the flared portion. Once dehydrated, hydrophilic materials may be easily machined because they are rigid solids. After machining, the flared portion may be re-hydrated producing a flared portion that is soft and pliable. An elastic member such as a ring or a plurality of collapsible spokes supported by a central hub may then be glued or mechanically attached to the wall of the flared portion. Alternatively, a material that changes its mechanical characteristics with temperature instead of hydration may also be used to machine the flared portion.

A manufacturer may also use standard injection molding techniques to create the flared portion. When the injection molding technique is utilized, the manufacturer places the elastic member within the mold near where the rim will be formed prior to injecting the material that forms the wall of the flared portion. When the wall material is injected, the elastic member becomes embedded within the rim.

Alternatively, a dip molding technique may be used to manufacture the flared portion. Referring to FIG. 7, a manufacturer dips a solid mold 700 into a bath of liquid polymer such as, for example, liquid silicone. Once the manufacturer removes the mold from the bath, the liquid polymer solidifies around the solid mold 700. A valve that controls the directional flow of urine may easily be produced within the flared portion using this technique, if a slit 710 is cut within the solid mold 700. The manufacturer may loosely attach an elastic member such as a loop of an elastic material or a plurality of spokes to the mold such that the elastic member becomes embedded within the flared portion during manufacturing.

In operation, the retaining portion of the ureteral stent is inserted through the urethra and advanced through the bladder and ureter and placed within the kidney. Prior to insertion, the retaining portion, if a coil is temporarily straightened and the flared portion is temporarily collapsed for insertion into the patient's body.

The coil may be straightened over a guidewire, which slides within the lumen of the ureteral stent and is sufficiently stiff to hold the curl in a straight configuration when placed within the ureteral stent. Alternatively, if other retention devices other than a coil are used as the retaining portion, they are placed in an insertion configuration, for example, hooks are straightened and malecots are collapsed. Prior to insertion into the body, the flared portion may be collapsed by placement of the entire ureteral stent within a cystoscope or a sheath. The inner diameter of the cystoscope should be substantially similar to the outer diameter of the elongated member, and thus when the ureteral stent is placed within the cystoscope or sheath, the flared portion would be in a collapsed configuration.

To position the ureteral stent within the urinary tract of a patient, a medical professional, such as a physician inserts the guidewire into the patient's urethra and advances the guidewire until a distal end of the guidewire is within the kidney. Once the guidewire is properly placed with its distal end within the kidney and its proximal end external to the body of the patient, the physician slides the cystoscope or sheath over the guidewire. Then the physician slides a ureteral stent in accordance with the present invention over the proximal end of the guidewire such that the guidewire, the cystoscope, and the ureteral stent all have the same central axis and that ureteral stent is radially positioned between the cystoscope and the guidewire. The physician may use a pusher to advance the ureteral stent through the urinary tract until the proximal end of the elongated portion is located within the kidney. At this point, the flared portion should be within the bladder because the length of the elongated portion is substantially equivalent to the length of the ureter, which connects the kidney to the bladder. Once the retaining portion is positioned within the kidney and the flared portion is within the bladder, the cystoscope and the guidewire are withdrawn, thereby allowing the retaining portion to re-coil and the flared portion to expand.

Variations, modifications, and other implementations of what is described herein will occur to those of ordinary skill in the art without departing from the spirit and the scope of the invention. The invention is not to be limited only to the preceding illustrative description.

What is claimed is:

1. A ureteral stent, comprising:
    an elongated portion defining a lumen and including a length;
    a retention portion extending from one end of the elongated portion, defining an interior space in communication with the lumen;
    a flared portion curving outward while extending from the other end of the elongated portion, the flared portion being collapsible into a collapsed state, the flared portion comprising an elastic member maintaining the shape of the flared portion in an expanded state, the elastic member having a plurality of collapsible spokes, said spokes being attached at a first end to the flared portion and at a second end to a hub, said spokes extending radially from said hub in the expanded state and extending longitudinally from said hub in the collapsed state.

2. The ureteral stent of claim 1, wherein said hub is substantially circular in shape.

3. The ureteral stent of claim 1, wherein said spokes are substantially linear.

4. The ureteral stent of claim 1, wherein said spokes are made of at least one of a shape-memory alloy and a superelastic material.

5. A ureteral stent, comprising:
    an elongated member having a side wall that defines a lumen, the elongated member including a distal end portion and a proximal end portion,
    the distal end portion including a retention member,
    the proximal end portion including a flared portion, the flared portion including a hub, a first spoke, and a second spoke, the first spoke having a first end portion coupled to the side wall and a second end portion coupled to the hub, the second spoke having a first end portion coupled to the side wall and a second end portion coupled to the hub.

6. The ureteral stent of claim 5, wherein the first spoke and the second spoke extend radially from the hub.

7. The ureteral stent of claim 5, wherein the flared portion has an expanded configuration and a collapsed configuration, the first spoke and the second spoke extend radially from the hub when the flared portion is in the expanded configuration, the first spoke and the second spoke extend longitudinally from the hub when the flared portion is in the collapsed configuration.

8. The ureteral stent of claim 7, wherein the first spoke and the second spoke are disposed within a plane in said expanded configuration.

9. The ureteral stent of claim 5, further comprising:
    a third spoke having a first end portion coupled to the side wall and a second end portion coupled to the hub.

10. The ureteral stent of claim 5, wherein the flared portion has an expanded configuration and a collapsed configuration, the lumen is configured to convey urine in a direction from the kidney to the bladder, the first spoke extends in a direction substantially orthogonal to the direction of the conveyance of urine when the flared portion is in the expanded configuration, the first spoke extends in a direction substantially parallel to the direction of the conveyance of urine when the flared portion is in the collapsed configuration.

11. The ureteral stent of claim 5, wherein the hub is substantially circular in shape.

12. The ureteral stent of claim 5, wherein the first spoke is substantially linear.

13. The ureteral stent of claim 5, wherein the first spoke is made of at least one of a shape-memory alloy and a superelastic material.

14. The ureteral stent of claim 5, wherein the hub, the first spoke, and the second spoke are configured to retain the flared portion in its expanded configuration when the flared portion is located within the bladder of the patient.

15. A method of disposing at least a portion of a ureteral stent within a bladder of a patient, the ureteral stent having an elongate portion and a flared portion, the flared portion including a hub, a first spoke, and a second spoke, the first spoke including a first end portion coupled to the hub and a second end portion coupled to the elongate portion, the second spoke including a first end portion coupled to the hub and a second end portion coupled to the elongate portion, comprising:

positioning the first spoke and the second spoke such that the first spoke and the second spoke generally extend longitudinally and the second end portion of the first spoke is disposed a first distance from the second end portion of the second spoke;

inserting at least a portion of the ureteral stent into the bladder of the patient; and repositioning the first spoke and the second spoke such that the second end portion of the first spoke is disposed a second distance from the second end portion of the second spoke, the first distance being smaller than the second distance.

16. The method of claim 15, wherein the positioning the first spoke and the second spoke includes moving the hub from a position proximate a bladder end portion of the ureteral stent in a direction towards a kidney end portion of the ureteral stent.

17. The method of claim 15, further comprising:

inserting at least a portion of the ureteral stent into a kidney of the patient.

\* \* \* \* \*